United States Patent [19] [11] 3,941,706
Goto et al. [45] Mar. 2, 1976

[54] FUNCTIONAL LIQUID

[75] Inventors: Kuniaki Goto, Tokyo; Tatsuo Sakashita, Yokohama, both of Japan

[73] Assignee: Nippon Zeon Co., Ltd., Tokyo, Japan

[22] Filed: June 13, 1974

[21] Appl. No.: 479,162

[30] Foreign Application Priority Data
June 20, 1973   Japan ............................... 48-69418

[52] U.S. Cl. ................ 252/59; 252/73; 260/668 R
[51] Int. Cl.² C10M 1/16; C10M 3/10; C10M 5/08; C10M 7/12
[58] Field of Search ............. 252/59, 73; 260/668 R

[56] References Cited
UNITED STATES PATENTS
| | | | |
|---|---|---|---|
| 3,597,358 | 8/1971 | Duling et al. | 252/73 |
| 3,786,106 | 1/1974 | Zuech et al. | 260/668 R |

FOREIGN PATENTS OR APPLICATIONS
| | | | |
|---|---|---|---|
| 886,603 | 1/1962 | United Kingdom | 260/668 R |

*Primary Examiner*—Delbert E. Gantz
*Assistant Examiner*—I. Vaughn
*Attorney, Agent, or Firm*—Bucknam and Archer

[57] ABSTRACT

A functional liquid for use as a heat transfer medium, anti-freezing liquid, insulating oil or the like, comprising at least one of dicyclopentylalkylbenzenes as the base.

3 Claims, No Drawings

FUNCTIONAL LIQUID

This invention relates to a novel functional liquid and more particularly it relates to a novel functional liquid comprising at least one dicyclopentylalkylbenzene as the base material.

Polychlorinated diphenyls, diphenyl ether, alkylnaphthalenes, alkylbenzenes, triaryldimethane, mineral and the like have heretofore been known as examples of organic compounds which may be used as functional liquids such as a heat transfer medium, antifreezing fluid, working fluid, insulating oil and vaporization preventing fluid. Among these compounds polychlorinated diphenyls have been widely used as one of the most excellent functional liquids in various industrial fields. However, the use of polychlorinated diphenyls has recently raised a serious social problem as to the environmental pollution caused thereby. Thus, attempts have been expedited to obtain less poisonous functional liquids in substitution for polychlorinated diphenyls. Among diphenyl type compounds other than polychlorinated diphenyls, and alkylnaphthalene type compounds, there are many which have a relatively low boiling point of 240° - 280°C as well as a relatively high pour point of about −10°C, and they are therefore disadvantageous in that they when used at high temperatures will produce their vapor pressure that is high, they will solidify in cold climates and they are not necessarily satisfactory in thermal stability, lubricating properties and the like.

Intense studies had been made by the present inventors in an attempt to reduce or eliminate the various drawbacks of the conventional functional liquids and, as a result, it has been found that alkylbenzene derivatives wherein two cyclopentyl groups are attached to the benzene nucleus, have a high boiling point and low pour point thereby rendering them adapted for use as a functional liquid, thus accomplishing this invention.

It is the primary object of this invention to provide novel functional liquids which are odorless and are excellent in thermal stability, oxidation resistance, low-temperature properties, electrical insulation and lubricating properties.

The functional liquid of this invention is a compound which is prepared by introducing two cyclopentyl groups to the benzene nucleus of a lower alkyl-substituted benzene such as toluene and ethyl benzene. Typical of the compounds for use as the functional liquid are dicyclopentyltoluene, dicyclopentylethylbenzene and dicyclopentylcumene, dicyclopentyltoluene being the most preferable.

The lower-alkylbenzene derivatives which may be used in this invention may easily be prepared by reacting an alkylbenzene with cyclopentene in the presence of a Friedel-Crafts type catalyst such as aluminum chloride or aluminum bromide. To this end, the cyclopentene may be substituted by a cyclopentyl halide or may be replaced by cyclopentadiene followed by hydrogenation. However, the process for the preparation of dicyclopentylalkylbenzenes according to this invention is not limited to these processes mentioned above. In this reaction toluene or ethyl benzene may be used with toluene being particularly preferred.

The alkylbenzene derivatives which may be used in this invention are each a compound which is a non-viscous liquid at room temperatures and has a boiling point of not lower than 300°C and a pour point of not higher than −50°C. It is considered that functional liquids of a high boiling point generally have a high pour point and, on the contrary, functional liquids of a low pour point generally have a low boiling point. It is unexpected and specific, however, that the functional liquid of this invention has a boiling point of as high as 300°C or higher, while it has a pour point of as low as −50°C or lower.

The compounds having these boiling and pour points will not be obtained unless two cyclopentyl groups are introduced to the benzene nucleus. For example, the introduction of one or three cyclopentyl groups to the benzene nucleus will not give products having satisfactory boiling and pour points; more particularly, the compounds containing one cyclopentyl group have low pour and boiling points, while those containing three cyclopentyl groups have high pour and boiling points, thus proving these compounds having less or more than two cyclopentyl groups to be unsuitable for use as a functional liquid according to this invention. The introduction of cyclohexyl groups in substitution for cyclopentyl groups will give a product having a too high pour point thereby rendering it unsuitable as a functional liquid according to this invention.

The functional liquid of this invention when heated to high temperatures will produce its vapor pressure that is low since it has a high boiling point. In addition the liquid is stable against thermal decomposition, excellently stable against oxidation, and substantially odorless. Furthermore, since the liquid has a pour point of −50°C or lower, it will have a low viscosity without solidification in cold climates. Thus, heat exchangers using such functional liquid as the heat transfer medium are advantageous in that they may rapidly resume their operation even after discontinuance of the operation thereof.

The functional liquid of this invention may also be used as a refrigerant because of its low pour point. It is useful as a high boiling solvent because of its high flash point and excellent compatibility with various organic materials. It is further useful as an insulation oil because of its excellent insulation, useful as a base oil for lubricating oils and grease because of its excellent lubricating properties, useful as an additive for other lubricating oils because of its capability of enhancing the viscosity index of the other lubricating oils and lowering the pour point thereof and useful as an antifreezing liquid, operating liquid and vaporization-preventing fluid.

This invention will be better understood by the following Reference examples and Working example wherein all parts are by weight unless otherwise specified.

Reference example 1

One hundred parts of n-heptane were incorporated with a catalytic amount of aluminum chloride and the resulting mixture allowed gaseous hydrogen chloride to be blown thereinto, after which the mixture was incorporated with 100 parts of toluene and 148 parts of cyclopentene and the whole was then reacted to produce a reaction mixture. The reaction mixture so produced was washed with water and distilled under reduced pressure to obtain a fraction boiling at temperatures from 320° to 327°C (at 760 mmHg).

This fraction was tested for its molecular weight and analyzed by means of infra-red ray absorption spectra with the result that the fraction was found to be dicyclopentyltoluene wherein two cyclopentyl groups are introduced into the benzene nucleus. The yield of dicyclopentyltoluene was at least 85% of the theoretical amount based on the amount of cyclopentene used.

Reference example 2

One hundred parts of n-heptane were incorporated with a catalytic amount of aluminum chloride, allowed gaseous hydrogen chloride to be blown thereinto and then incorporated with 115 parts of ethyl benzene and 148 parts of cyclopentene. The resulting mixture was subjected to reaction to form a reaction mixture which was washed with water and then distilled under reduced pressure thereby obtaining a fraction boiling at 330° – 335°C (760 mmHg). This fraction was tested for its molecular weight and then analyzed by means of infra-red ray absorption spectra thereby to find that the fraction was dicyclopentylethylbenzene wherein two cyclopentyl groups are introduced into the benzene nucleus. The yield of dicyclopentylethylbenzene was at least 80% of the theoretical amount based on cyclopentene used.

Example

Dicyclopentyltoluene (Sample A) and dicyclopentylethylbenzene (Sample B) respectively prepared in Reference examples 1 and 2 were tested for their properties and further for their performances as a functional fluid. For comparison, commercially available functional fluids which have heretofore been generally used were likewise tested. The results are as follows.

(1) External appearance

| Sample A | Colorless, transparent (Hazen number, 10 or less) and odorless (at room temperatures) oily material |
| --- | --- |
| Sample B | The same as above |

(2) Specific gravity and Refractive index

| | Sp. gr. ($d_4^{20}$) | Ref. index ($n_D^{20}$) |
| --- | --- | --- |
| Sample A | 0.970 | 1.5383 |
| Sample B | 0.963 | 1.5357 |

(3) Acid value

| | Acid value (JIS-K 2501) |
| --- | --- |
| Sample A | 0.00 mg KOH/g |
| Sample B | 0.00 |

(4) Viscosity

| | |
| --- | --- |
| Sample A | 14.7 cst (at 20°C) |
| Sample B | 18.2 cst (at 20°C) |

(5) Boiling point, Pour point and Flash point

| | Boiling point (converted at 760 mmHg) | Pour point | Flash point (C.O.C.) |
| --- | --- | --- | --- |
| Sample A | 320 – 327°C | −60°C or lower | 168°C |
| Sample B | 330 – 335°C | −50°C or lower | 178°C |
| KSK-oil[*1] No. 260 | 268°C | −50°C or lower | 120°C |
| KSK-oil No. 330 | 323°C | −30°C or lower | 165°C |
| Therm S 600[*2] | 286°C | −10°C | 148°C |
| Kanechlor[*3] | 325 – 360°C | −19 – −15°C | None |
| Therm S 900[*4] | 340°C or higher | −10°C or lower | 178°C |
| Marlotherm-S[*5] | 390°C | −35°C | 190°C |

[*1]: Commercially available alkylnaphthalene type compound (produced by Soken Kagaku Co., Ltd.).
[*2]: Commercially available diphenyl type compound (produced by Shin Nippon Seitetsu Kagaku Co., Ltd.).
[*3]: Commercially available polychlorinated diphenyl type compound (produced by Kanegafuchi Kagaku Co., Ltd.).
[*4]: Commercially available triphenyl derivative type compound (produced by Shin Nippon Seitetsu Kagaku Co., Ltd.).
[*5]: Commercially available triaryldimethane type compound (produced by Huls Co., Ltd.).

The conventional functional liquids which have heretofore been marketed tend to have a higher pour point as they have a higher boiling point, while the functional liquids of this invention have a boiling point of as high as 300°C or higher, a pour point of as low as −50°C or lower and a relatively high flash point which is nearly equal to that of commercially available functional liquids having a high boiling point.

(6) Residual carbon (Measured by the Conradson method prescribed in JIS-K 2270)

| Sample A | not more than 0.01 wt.% |
| --- | --- |
| Sample B | not more than 0.01 wt.% |

(7) Copper plate corrosion test (100°C, 3 hours) in accordance with JIS K-2513

| Sample A | not more than 1 |
| --- | --- |
| Sample B | not more than 1 |

(8) Compatibility

Samples A and B were each mixed with each of the following compounds to find their compatibility. The results are shown below, and Samples A and B exhibited quite the same compatibility.

| | |
| --- | --- |
| Water | X |
| Methanol | X |
| Ethanol | X |
| n-Propanol | O |
| n-Butanol | O |
| iso-Butanol | O |
| Ethylene glycol | X |
| Trimethylolpropane | X |
| Acetic acid | X |
| Acetic anhydride | X |
| Caprylic acid | O |
| Acrylic acid | O |
| Methacrylic acid | O |
| Stearic acid | O |
| Cinnamic acid | O |
| Maleic acid | X |
| Fumaric acid | X |
| Phthalic acid | X |
| Terephthalic acid | X |
| Benzoic acid | O |
| Acetone | O |
| Methyl ethyl ketone | O |
| Ethyl acetate | O |
| Methyl acrylate | O |
| Ethyl acrylate | O |
| Pyridine | O |
| Hexamethylenediamine | O |
| Dimethyl formamide | O |

-continued

| | |
|---|---|
| Olive oil | ○ |
| Phenol | ○ |
| p-Cresol | ○ |
| Gasoline | ○ |
| Petroleum ether | ○ |
| Benzene | ○ |
| Toluene | ○ |
| Xylene | ○ |
| Carbon tetrachloride | ○ |
| Chloroform | ○ |
| Methylene chloride | ○ |
| Ethylene dichloride | ○ |

Note: ○ Very soluble at room temperatures.
◯ Soluble at room temperatures.
X Insoluble or almost insoluble at room temperatures.

heating of the Sample A was found to be not corroded at all after the test, from which it is seen that the Sample had a very excellent oxidation stability.

(10) Heat stability

Three hundred and fifty grams of Sample A (oil) were charged in a 500-ml autoclave made of a stainless steel (SUS-32) and heated to 350°C in an atmosphere of nitrogen. After kept under this condition for 520 hours the Sample A was cooled and tested for various properties; and the aforesaid procedure was followed except that the heating is effected for 1040 hours. The following Table shows a comparison of the properties between the original Sample A (before the heating), Sample A (after the 520 hours' heating) and Sample A (after the 1040 hours' heating).

Table

| | Sample A original, before heating | Sample A after 520 hrs' heating | Sample A after 1040 hrs' heating |
|---|---|---|---|
| Exterior appearance | Colorless, transparent | Slightly light-yellow | Light-yellow |
| Odor (at room temp.) | None | None | Almost none |
| Deposit (at room temp.) | None | None | None |
| Specific gravity ($d_4^{20}$) | 0.970 | 0.970 | 0.972 |
| Refractive index ($n_D^{20}$) | 1.5383 | 1.5383 | 1.5394 |
| Acid value (mg KOH/g) | 0.00 | 0.01 | 0.01 |
| Viscosity (cst, at 20°C) | 14.7 | 15.1 | 19.4 |
| Residual carbon (wt.%) | 0.01 or less | 0.01 or less | 0.03 |
| Copper plate corrosion test | 1 or less | 1 or less | 1 or less |
| Naphtha-insoluble matter (at room temp.) | None | None | None |
| Flash point (°C) | 168 | 165 | 164 |
| Variation in pressure during test ($Kg/cm^2$) | | | |
| at 30°C | 0 | 0.4 | 1.5 |
| at 350°C | 1.1 | 1.8 | 2.6 |
| Rate of decomposition gas produced* (mol gas/mol oil, hr) | — | $5.4 \times 10^{-6}$ | $1.3 \times 10^{-5}$ |
| Rate of degradation** (vol.%/100 hrs) | — | 2.0 | |

*Rate of gases produced from the Sample A by thermal decomposition during the test and still remaining gaseous at room temperatures.
**Rate of new fractions produced from the Sample A during the heating test and boiling at temperatures outside the boiling point range of the original Sample A.

(9) Oxidation stability (Stability against oxidation)

Sample A which was not incorporated with an anti-aging agent, was heated to 120°C for 75 hours in an oxygen atmosphere in the presence of a copper catalyst to find its oxidation stability. For comparison, a commercially available alkylnaphthalene type compound (KSK-oil No. 260) and a commercially available diphenyl type compound (Therm S 600) were subjected to the same test as above. The results are indicated in the following Table.

Table

| Sample | Condition after test Increment of acid value (mg KOH/g) | Gardner color | Sludge formed (wt.%) |
|---|---|---|---|
| Sample A | 0.30 | 5 | 0.09 |
| KSK-oil No. 260 | 0.42 | 15 | 0.20 |
| Therm S 600 | 0.50 | 12 | 0.14 |

It is seen from this Table that the Sample A had a smaller increment of acid value, formed sludge in a smaller amount and was found less colored after the end of the test than the commercially available functional liquids although said Sample did not contain an anti-aging agent. The copper used as the catalyst in the For comparison, a commercially available triaryldimethane type compound (Marlotherm-S produced by Hüls Co., Ltd.) which has heretofore been recommended as a functional liquid having a high boiling point was heated for 520 hours in the same manner as above to find its rate of decomposition gas produced and rate of degradation with the respective results of $7.2 \times 10^{-5}$ mol gas/mol oil, hr and 8.0 vol. %. On the other hand, Sample A was heated to 380°C for 520 hours to find its rate of decomposition gas produced with the result of $3.4 \times 10^{-5}$ (mol gas/mol oil, hr) which was lower than that obtained with said commercially available compound by heating to 350°C. From the foregoing it will be understood that the Sample A is superior in heat stability.

(11) Electrical properties

In accordance with the method prescribed in JIS-C 2320 (Insulating oil), Samples A and B were respectively tested at 80°C and 50 Hz for their dielectric loss tangent, further tested at 80°C and under a condition of 2.5 mm in distance between the electrodes for their dielectric breakdown strength and still further tested at 80°C for their volume resistivity. The values obtained are indicated in the following Table in which are also indicated, for comparison, the values required in Insulating Oil No. 1 prescribed in JIS (Japanese Industrial Standard) and those for conventional insulating oils (polychlorinated diphenyl type and polybutene type insulating oils).

conventional, commercially available functional liquids. Said specific compounds also exhibit excellent electrical and lubricating properties.

Table

|  | Dielectric loss tangent | Dielectric breakdown strength (KV) | Volume resistivity ($\Omega \cdot cm$) |
|---|---|---|---|
| Sample A | $1 \times 10^{-4}$ | 50 or higher | $2.2 \times 10^{14}$ |
| Sample B | $1 \times 10^{-4}$ | 50 or higher | $2.2 \times 10^{14}$ |
| Insulating Oil No. 1 | $2 \times 10^{-3}$ or less | 30 or higher | $1 \times 10^{13}$ or higher |
| Kanechlor No. 300 | $5 \times 10^{-3}$ | 50 or higher | not measured |
| Idemitsu polybutene 15R* | $2 \times 10^{-4}$ | 50 or higher | $8.0 \times 10^{14}$ |

*Commercially available polybutene type compound (produced by Idemitsu Sekiyu Kagaku Co., Ltd.).

(12) Lubricating properties

In order to investigate the lubricating properties of Sample A, a portion of Sample A was tested for viscosity index in accordance with JIS K-2284, and another portion thereof was subjected to the four ball test for load carrying capacity and wear dint diameter in accordance with JIS K-2519, the four ball test being carried out at 20°C and 200 r.p.m. while increasing the pressure by 0.5 Kg/cm$^2$ per minute. The results are shown hereunder.

| Viscosity index | 80 |
|---|---|
| Load carrying capacity (Kg/cm$^2$) | 8.5 |
| Wear dint diameter (mm) | 1.34 |

In addition a portion of Sample A was added to a mineral oil type lubricating oil to find the properties thereof as an additive to a lubricating oil. The results are shown in the following Table.

Table

| Amount of Sample A used Amount of mineral oil type lubricating oil (wt. ratio) | 0/100 | 10/90 | 20/80 | 30/70 |
|---|---|---|---|---|
| Viscosity index | 104 | 115 | 124 | 131 |
| Viscosity (cst) 37.78°C | 223.5 | 144.7 | 98.1 | 67.2 |
| 98.89°C | 19.2 | 15.6 | 12.7 | 10.1 |
| Pour point (°C) | −55 | −57 | −59 | −61 |

Sample A has, per se, excellent properties as a lubricating oil and is further capable of improving other lubricating oils in lubricating properties by adding the Sample A thereto.

From these results it is seen that dicyclopentylalkylbenzenes are specific compounds which have a high boiling point and, at the same time, a low pour point, and that they further have the following features. These specific compounds are very satisfactorily compatible with various organic materials and have much more excellent oxidation stability and heat stability than the As mentioned above dicyclopentylalkylbenzenes are suitable as a functional liquid because of their various properties or features, and they are used as a heat transfer medium, insulating oil, lubricating agent, solvent having a high boiling point, working fluid or the like.

What is claimed is:

1. A functional liquid consisting essentially of at least one organic compound which is a dicyclopentylalkylbenzene represented by the following formula

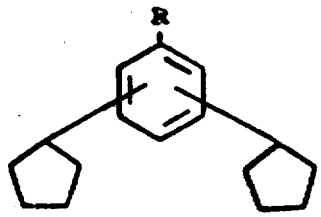

wherein R is an alkyl group having 1 to 3 carbon atoms.

2. A functional liquid according to claim 1, wherein the dicyclopentylalkylbenzene has a boiling point of not lower than 300°C and a pour point of not higher than −50°C.

3. A functional liquid according to claim 1, wherein the dicyclopentylalkylbenzene is a member selected from the group consisting of dicyclopentyltoluene and dicyclopentylethylbenzene.

* * * * *